(12) United States Patent
Yamazaki

(10) Patent No.: US 8,659,648 B2
(45) Date of Patent: Feb. 25, 2014

(54) ENDOSCOPE APPARATUS

(75) Inventor: Kenji Yamazaki, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 73 days.

(21) Appl. No.: 13/299,801

(22) Filed: Nov. 18, 2011

(65) Prior Publication Data

US 2012/0127293 A1    May 24, 2012

Related U.S. Application Data

(63) Continuation of application No. PCT/JP2011/063063, filed on Jun. 7, 2011.

(30) Foreign Application Priority Data

Jun. 24, 2010 (JP) .................................. 2010-144083

(51) Int. Cl.
*H04N 7/18* (2006.01)

(52) U.S. Cl.
USPC ................... 348/71; 348/76; 348/68; 348/70; 348/65; 600/109; 600/160; 600/112; 600/178; 600/181; 600/101

(58) Field of Classification Search
USPC ............ 348/71, 76, 68, 70, 65; 600/109, 160, 600/112, 178, 181, 101
See application file for complete search history.

(56) References Cited

U.S. PATENT DOCUMENTS

| | | | |
|---|---|---|---|
| 7,393,321 B2 * | 7/2008 | Doguchi et al. | 600/109 |
| 7,670,286 B2 * | 3/2010 | Imaizumi et al. | 600/160 |
| 7,889,228 B2 * | 2/2011 | Ishihara et al. | 348/65 |
| 2005/0068427 A1 | 3/2005 | Sudo et al. | |
| 2006/0211915 A1 * | 9/2006 | Takeuchi et al. | 600/109 |
| 2009/0036741 A1 * | 2/2009 | Igarashi et al. | 600/160 |
| 2009/0066787 A1 * | 3/2009 | Yamazaki | 348/70 |
| 2009/0141125 A1 | 6/2009 | Yamazaki | |
| 2009/0156901 A1 * | 6/2009 | Gono | 600/180 |

FOREIGN PATENT DOCUMENTS

| | | |
|---|---|---|
| EP | 2 005 877 A2 | 12/2008 |
| EP | 2 047 792 A1 | 4/2009 |
| JP | 2000-209605 | 7/2000 |
| JP | 2000-221417 | 8/2000 |
| JP | 2004-321608 | 11/2004 |
| JP | 2007-300972 | 11/2007 |
| JP | 2008-036035 | 2/2008 |
| WO | WO 2008/015826 A1 | 2/2008 |

OTHER PUBLICATIONS

European Search Report dated Jun. 25, 2013 from corresponding European Patent Application No. 11 79 7985.6.

* cited by examiner

*Primary Examiner* — Shawn An
(74) *Attorney, Agent, or Firm* — Scully, Scott, Murphy & Presser, P.C.

(57) ABSTRACT

In an endoscope apparatus, a first color separation section separates an image picked up by an image pickup section into a first luminance signal and a first color difference signal, then a first color conversion section and a second color separation section convert the first luminance signal and the first color difference signal to first three primary color signals and second three primary color signals respectively, a signal intensity ratio calculation circuit calculates a signal intensity ratio among the first three primary color signals, matrix coefficients of the second color separation section are changed based on the calculated signal intensity ratio and the second color separation section converts the first luminance signal and the second color difference signal to the second three primary color signals.

10 Claims, 9 Drawing Sheets

ENDOSCOPE APPARATUS

CROSS REFERENCE TO RELATED APPLICATION

This application is a continuation application of PCT/JP2011/063063 filed on Jun. 7, 2011 and claims benefit of Japanese Application No. 2010-144083 filed in Japan on Jun. 24, 2010, the entire contents of which are incorporated herein by this reference.

BACKGROUND OF THE INVENTION

1. Field of the Invention

The present invention relates to an endoscope apparatus that performs signal processing on image pickup means provided in an endoscope and generates an endoscope image.

2. Description of the Related Art

In recent years, electronic endoscopes equipped with image pickup means are widely used in various endoscope inspections or the like.

When performing an endoscope inspection using an electronic endoscope, various endoscope apparatuses are available such as a simultaneous type endoscope apparatus that picks up a color image using an image pickup device provided with a color optical filter under illumination of white light and a frame-sequential endoscope apparatus that picks up a color image under frame-sequential illuminating light of R, G and B using a monochrome image pickup device, and these endoscope apparatuses have different signal processing systems.

A conventional example in Japanese Patent Application Laid-Open Publication No. 2007-300972 discloses a simultaneous type endoscope apparatus. The conventional example in FIG. 1 adopts an endoscope having image pickup means provided with a complementary color filter and a signal processing apparatus for this image pickup means separates a luminance signal Y and a color signal C through a Y/C separation circuit.

Furthermore, this signal processing apparatus generates a luminance signal Yl obtained by passing the luminance signal Y through a low pass filter and a luminance signal Yh without the luminance signal Y passing through a low pass filter.

Furthermore, this signal processing apparatus adopts a configuration in which a selector 39 selects the luminance signal Yh or a luminance signal Ynbi in an observation mode of NBI outputted from a second matrix circuit 46 and outputs the selected signal to a next stage in conjunction with switching between observation modes of normal white light imaging (WLI) and narrow band imaging (NBI).

SUMMARY OF THE INVENTION

An endoscope apparatus according to one aspect of the present invention includes an image pickup section that picks up an image of a body cavity interior, a first color separation section that separates the image picked up by the image pickup section into a first luminance signal and a first color difference signal, a first color conversion section that converts the signals to first three primary color signals based on the first luminance signal and the first color difference signal, a second color conversion section that converts an output signal from the first color conversion section to a second color difference signal, a second color separation section that performs color separation matrix calculation on the first luminance signal and an output signal from the second color conversion section to convert the signals to second three primary color signals and a signal intensity ratio calculation section that calculates an intensity ratio among the first three primary color signals outputted from the first color conversion section, wherein matrix coefficients used for the matrix calculation of the second color separation section are changed based on the intensity ratio of the first three primary color signals calculated by the signal intensity ratio calculation section and the second color separation section converts the first luminance signal and the second color difference signal to the second three primary color signals.

DETAILED DESCRIPTION OF THE PREFERRED EMBODIMENTS

Hereinafter, embodiments of the present invention will be described with reference to the accompanying drawings.

(First Embodiment)

Figure 1:
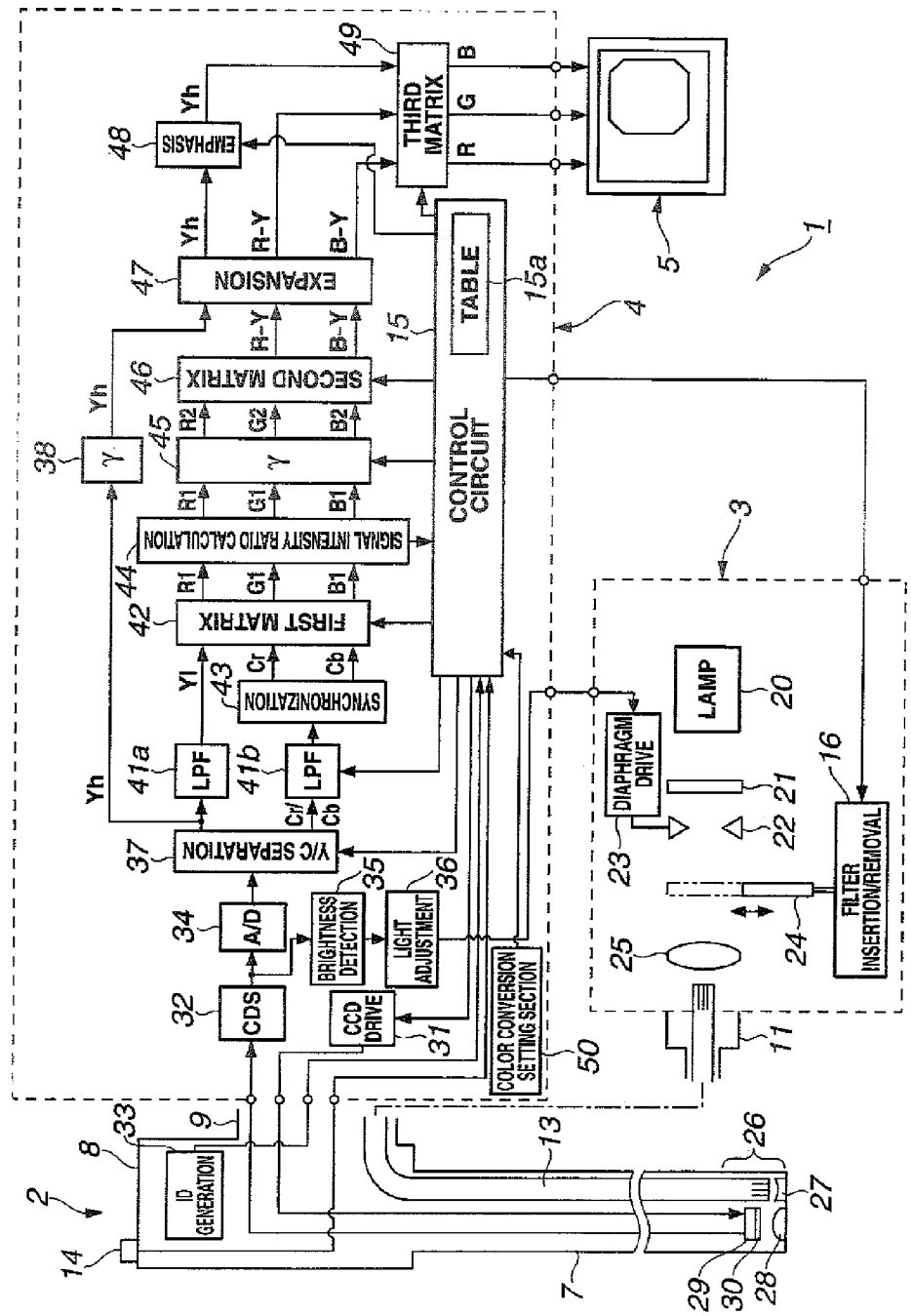
FIG. 1 is a block diagram illustrating a configuration of an endoscope apparatus according to a first embodiment of the present invention.

As shown in FIG. 1, an endoscope apparatus 1 according to a first embodiment is provided with an electronic endoscope (hereinafter simply abbreviated to "endoscope") 2 inserted into a body cavity to perform an endoscope inspection and a light source device 3 that supplies illuminating light to the endoscope 2. Furthermore, this endoscope apparatus 1 is also provided with a video processor 4 as an endoscope video signal processing apparatus that drives image pickup means incorporated in the endoscope 2 and performs signal processing on an output signal of the image pickup means and a monitor 5 that receives the video signal outputted from the video processor 4 as input and displays an image obtained by applying signal processing to the image picked up by the image pickup means as an endoscope image.

The endoscope 2 includes an elongated insertion portion 7, an operation section 8 provided at a rear end of the insertion portion 7 and a universal cable 9 that extends from the operation section 8, and a light guide connector 11 at an end of the universal cable 9 is detachably connected to the light source device 3, and a signal connector is detachably connected to the video processor 4.

A light guide 13 for transmitting illuminating light is inserted into the insertion portion 7 and illuminating light from the light source device 3 is supplied to the light guide 13 by connecting the light guide connector 11 at an end of the operator's hand side in the light guide 13 to the light source device 3.

The light source device 3 generates white illuminating light to cover a visible wavelength region as illuminating light and supplies the white illuminating light to the light guide 13 in a normal white light imaging (abbreviated to "WLI") mode.

On the other hand, in a narrow band imaging (abbreviated to "NBI") mode, the light source device 3 generates narrow band illuminating light as illuminating light and supplies the narrow band illuminating light to the light guide 13.

A changeover between the WLI mode and NBI mode can be instructed using, for example, a mode changeover switch 14 made up of a scope switch or the like provided at the operation section 8 of the endoscope 2. The mode changeover switch 14 may be made up of not only the scope switch provided for the endoscope 2 but also a foot switch or the mode changeover switch may be provided on the front panel of the video processor 4 or may be made up of a keyboard (not shown).

A changeover signal from the mode changeover switch 14 is inputted to a control circuit 15 in the video processor 4 and when the changeover signal is inputted, the control circuit 15 controls a filter insertion/removal mechanism 16 of the light source device 3 to selectively switch between normal white light and narrow band illuminating light.

Furthermore, as will be described later, this control circuit 15 also performs control of changing characteristics of the signal processing system in the video processor 4 operating in conjunction with the changeover control of illuminating light supplied from the light source device 3 to the light guide 13. Signal processing suitable for the respective observation modes of the WLI mode and NBI mode can be performed by changing characteristics of the signal processing system through a changeover operation using the mode changeover switch 14.

The light source device 3 incorporates a lamp 20 that generates illuminating light and this lamp 20 generates illuminating light including a visible wavelength region. With infrared light thereof cut by an infrared cut filter 21, the illuminating light is converted to illuminating light of a wavelength close to a wavelength band of quasi-white light and then impinged on a diaphragm 22. The aperture of the diaphragm 22 is adjusted by a diaphragm drive circuit 23 and the quantity of light passing therethrough is thereby controlled.

The illuminating light that passes through the diaphragm 22 is condensed by a condensing lens 25 after passing through a narrow band filter 24 which is inserted/removed into/from an illuminating light path by the filter insertion/removal mechanism 16 made up of a plunger or the like in the NBI mode or without passing through the narrow band filter 24 in the WLI mode, and made to impinge on an end face on the operator's hand side of the light guide 13, that is, on the incident end face.

Figure 2:
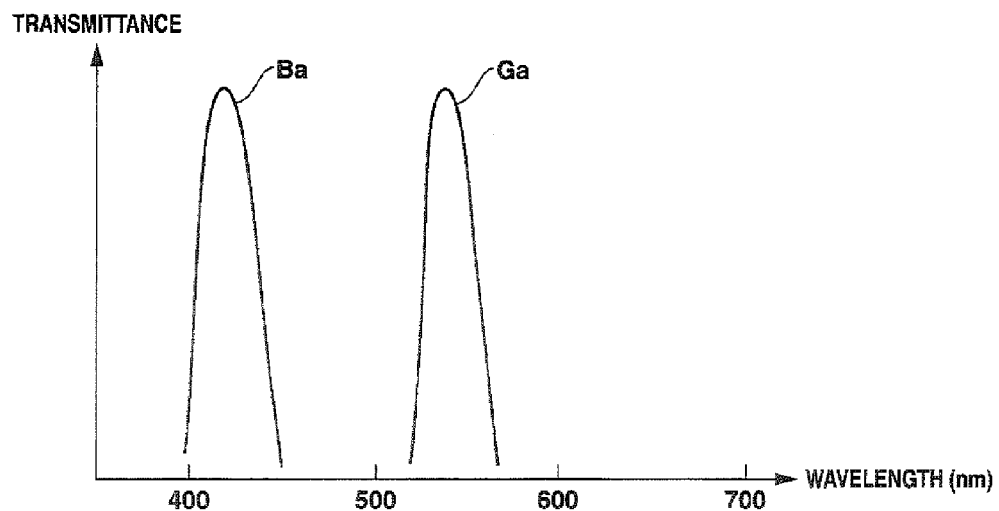
FIG. 2 is a characteristic diagram illustrating a spectral characteristic example of a narrow band filter.

FIG. 2 shows an example of spectral characteristics of the narrow band filter 24. The narrow band filter 24 shows two-peak filter characteristics and has, for example, narrow band pass filter characteristic portions Ga and Ba in wavelength regions of green (G) and blue (B) respectively.

To be more specific, the narrow band pass filter characteristic portions Ga and Ba have center wave lengths of 540 nm and 420 nm respectively and band pass characteristics having a full width at half maximum of 20 to 40 nm.

Therefore, when the narrow band filter 24 is placed in the illuminating light path, two bands of narrow band illuminating light that have passed through the narrow band pass filter characteristic portions Ga and Ba are made to impinge on the light guide 13.

On the other hand, when the narrow band filter 24 is not placed in the illuminating light path, wide band white light is supplied to the light guide 13.

The illuminating light from the light guide 13 is transmitted to a front end face thereof through the light guide 13, outputted via an illumination lens 27 making up illumination means attached to an illuminating window provided at a distal end portion 26 of the insertion portion 7 and radiated onto the surface of a living tissue such as a diseased part in the body cavity.

An observation window is provided adjacent to the illuminating window at the distal end portion 26 and an objective lens 28 is fitted into the observation window. This objective lens 28 forms an optical image from reflected light from the living tissue. A charge coupled device (abbreviated to "CCD") 29 as a solid image pickup device making up image pickup means is placed at the image forming position of the objective lens 28 and the optical image is photoelectrically converted by the CCD 29.

Figure 3:
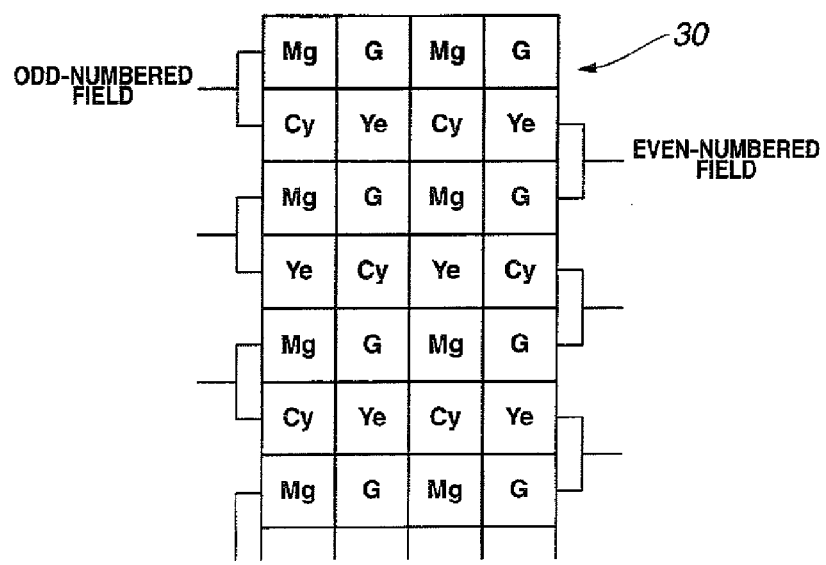
FIG. 3 is a diagram illustrating a configuration of a filter array of a color separation filter provided for a solid image pickup device.

For example, a complementary color filter as shown in FIG. 3 is mounted in pixel units on the image pickup surface of the CCD 29 as a color separation filter 30 that performs optical color separation.

In the complementary color filter, four color chips of magenta (Mg), green (G), cyan (Cy) and yellow (Ye) are arranged in front of each pixel, Mg and G are alternately arranged in the horizontal direction, and an array of Mg, Cy, Mg, Ye and an array of G, Ye, G, Cy are arranged sequentially in the vertical direction.

The CCD 29 using the complementary color filter adds up and sequentially reads two columns of pixels neighboring each other in the vertical direction, and reads pixels by shifting the columns of pixels between an odd-numbered field and an even-numbered field. From the signal read from the CCD 29, a Y/C separation circuit 37 (as first color separation means) located after the CCD 29 generates a luminance signal and a color difference signal, as is publicly known.

The above-described CCD 29 is connected to one end of the signal line and by connecting a signal connector to which the other end of the signal line is connected to the CCD 29 to the video processor 4, the CCD 29 is connected to a CCD drive circuit 31 and a CDS circuit 32 in the video processor 4.

Each endoscope 2 is provided with an ID generation section 33 that generates identification information (ID) specific to the endoscope 2, the ID from the ID generation section 33 is inputted to the control circuit 15 and the control circuit 15 identifies the type of the endoscope 2 connected to the video processor 4, the number and types or the like of pixels of the CCD 29 incorporated in the endoscope 2 using the ID.

The control circuit 15 then controls the CCD drive circuit 31 so as to appropriately drive the CCD 29 of the identified endoscope 2.

In the CCD 29, the image pickup signal photoelectrically converted with application of the CCD drive signal from the CCD drive circuit 31 is inputted to the correlation double sampling circuit (abbreviated to "CDS circuit") 32. A signal component is extracted by the CDS circuit 32 from the image pickup signal, converted to a baseband signal, then inputted to an A/D conversion circuit 34 to be converted to a digital signal, and also inputted to a brightness detection circuit 35 where brightness (average luminance of the signal) is detected.

The brightness signal detected by the brightness detection circuit 35 is inputted to a light adjustment circuit 36, where a light adjustment signal for adjusting light based on a difference from reference brightness (light adjustment target value) is generated. The light adjustment signal from this light adjustment circuit 36 is inputted to the diaphragm drive circuit 23 and the diaphragm drive circuit 23 adjusts the aperture of the diaphragm 22 so as to obtain the reference brightness.

The digital signal outputted from the A/D conversion circuit 34 is inputted to the Y/C separation circuit 37 and the Y/C separation circuit 37 generates a luminance signal Y and line-sequential color difference signals Cr and Cb (as a color signal C in a broad sense). The Y/C separation circuit 37 forms first color separation means, and therefore, the luminance signal Y as the output signal of the Y/C separation circuit 37 corresponds to a first luminance signal, and the color difference signals Cr and Cb correspond to first color difference signals.

The luminance signal Y is inputted to an expansion circuit 47 via a γ circuit 38 (this luminance signal is represented by "Yh") and also inputted to a first low pass filter (abbreviated to "LPF") 41a which limits the passband of the signal.

The LPF 41a is set to a wide passband in correspondence with the luminance signal Y and a luminance signal Yl of a band set by a passband characteristic of this LPF 41a is inputted to a first matrix circuit 42 as first color conversion means.

Furthermore, the color difference signals Cr and Cb are inputted to a (line-sequential) synchronization circuit 43 via a second LPF 41b that limits the passband of the signal.

In this case, the passband characteristic of the second LPF 41b is modified by the control circuit 15 according to the observation mode. To be more specific, in the WLI mode, the second LPF 41b is set to a lower band than the first LPF 41a. That is, in the WLI mode, the second LPF 41b is set so as to perform signal processing in conformity with a typical video signal standard.

On the other hand, in the NBI mode, the second LPF 41b is modified to a wider band than the low band in the WLI mode. For example, the second LPF 41b is set (modified) to a wide band in substantially the same way as the first LPF 41a.

Thus, the second LPF 41b forms processing characteristic modifying means for modifying the processing characteristic of limiting the passband with respect to the color difference signals Cr and Cb in conjunction with changeover of the observation mode.

By widening the signal passband characteristic of the second LPF 41b, it is possible to improve the resolution of the running state of a capillary vessel or the running state of a blood vessel close to the surface layer obtained by a color signal of G, an image of which is picked up under illuminating light of G close to the luminance signal from the narrow band pass filter characteristic portion Ga and obtain an image of high image quality, easy to diagnose.

The synchronization circuit 43 generates synchronized color difference signals Cr and Cb, and the color difference signals Cr and Cb are inputted to the first matrix circuit 42 as first color conversion means.

The first matrix circuit 42 converts the luminance signal Yl and the color difference signals Cr and Cb to three primary color signals R1, G1 and B1 and outputs the three primary color signals to a signal intensity ratio calculation circuit 44 that calculates a signal intensity ratio. Furthermore, the first three primary color signals R1, G1 and B1 are also inputted to a γ circuit 45 that performs gamma correction.

This first matrix circuit 42 is controlled by the control circuit 15 and the values of matrix coefficients (that determine the conversion characteristic) are modified (switched) according to the characteristic of the color separation filter 30 of the CCD 29 and the characteristic of the narrow band filter 24. That is, the first matrix circuit 42 modifies the values of the matrix coefficients to convert to the first three primary color signals R1, G1 and B1 according to the spectral characteristics of light incident on the CCD 29 as the image pickup means. The first matrix circuit 42 performs conversion to three primary color signals R1, G1 and B1 free of all or most of color mixture. As described above, since illuminating light of a red wavelength band is not used in the NBI mode, no color signal of R1 is provided.

For example, the characteristic of the color separation filter 30 of the CCD 29 mounted on the endoscope 2 may differ depending on the endoscope 2 actually connected to the video processor 4, and the control circuit 15 modifies the matrix coefficients to convert to the first three primary color signals R1, G1 and B1 through the first matrix circuit 42 according to the characteristic of the color separation filter 30 of the CCD 29 that is actually used based on the ID information.

By so doing, even when the type of the image pickup means actually used is different, it is possible to appropriately handle the difference, prevent the occurrence of false colors or perform conversion to first three primary color signals R1, G1 and B1 with little color mixture.

Furthermore, the signal intensity ratio calculation circuit 44 calculates signal intensity ratios s, t and u of the three primary color signals R1, G1 and B1 inputted via the first matrix circuit 42 and outputs information of the calculated signal intensity ratios s, t and u to the control circuit 15.

For this purpose, the signal intensity ratio calculation circuit 44 accumulates the respective signal levels of the first three primary color signals R1, G1 and B1 outputted from the first matrix circuit 42 in field units and calculates the respective signal intensity ratios s, t and u of the three primary color signals R1, G1 and B1 based on the accumulation result.

Figure 4:
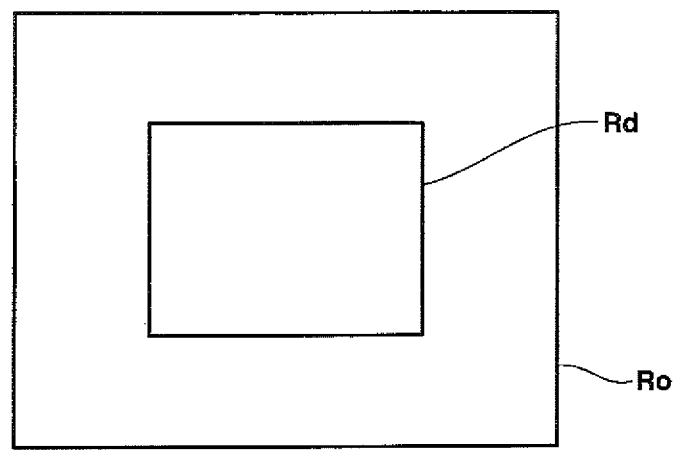
FIG. 4 is a diagram illustrating a predetermined region where a signal intensity ratio is calculated.

In this case, as shown, for example, in FIG. 4, the signal levels are accumulated within a predetermined region Rd set within an image region Ro of one field and the respective signal intensity ratios s, t and u are calculated. The signal intensity ratio calculation circuit 44 may be provided, for example, inside the control circuit 15.

Assuming the accumulation values of the three primary color signals R1, G1 and B1 in the predetermined region Rd are iR, iG and iB respectively, the signal intensity ratios s, t and u are:

$s=iR/(iR+iG+iB)$ $t=iG/(iR+iG+iB)$ $u=iB/(iR+iG+iB)$ which satisfies a condition of s+t+u=1. Therefore, instead of calculating the three s, t and u, two of the three may be calculated and the remaining one may be calculated from the condition of s+t+u=1.

Furthermore, because the color signal of R1 is 0 in the NBI mode, s=0. In this case, two of t and u may be calculated or one of the two may be calculated and the remaining one may be calculated from the condition of t+u=1.

In the present embodiment, the respective signal intensity ratios s, t and u of the three primary color signals R1, G1 and B1 are calculated in field units, and matrix coefficients of the third matrix circuit 49 making up the second color separation means are dynamically modified in field units as will be described later.

The control circuit 15 also incorporates a reference table 15a to be used for reference to set matrix coefficients by the first matrix circuit 42, a second matrix circuit 46 and a third matrix circuit 49.

The γ circuit 45 is also controlled by the control circuit 15. To be more specific, in the NBI mode, a γ characteristic is modified so as to emphasize γ correction characteristics compared with that in the WLI mode. This causes the contrast on the low signal level side to be emphasized and provides a display characteristic easier to identify.

Three primary color signals R2, G2 and B2 γ-corrected by this y circuit 45 are inputted to the second matrix circuit 46 making up the second color conversion means and converted to color difference signals R−Y and B−Y by the second matrix circuit 46 as shown below. Matrix Mat2 is expressed, for example, by Equation (3).

$$\begin{bmatrix} R-Y \\ B-Y \end{bmatrix} = Mat2 \cdot \begin{bmatrix} R2 \\ G2 \\ B2 \end{bmatrix} \quad (1)$$

This second matrix circuit 46 adopts, for example, matrix coefficients set to fixed values irrespective of a changeover between observation modes.

The color difference signals R−Y and B−Y outputted from the second matrix circuit 46 together with the luminance signal Yh are inputted to the expansion circuit 47 that performs expansion processing.

The luminance signal Yh subjected to expansion processing by the expansion circuit 47 is subjected to contour emphasis by the emphasis circuit 48, then inputted to the third matrix circuit 49, and the color difference signals R−Y and B−Y subjected to the expansion processing by the expansion circuit 47 are inputted to the third matrix circuit 49 without passing through the emphasis circuit 48.

The third matrix circuit 49 as the second color separation means converts the luminance signal Yh and the color difference signals R−Y and B−Y to three primary color signals R, G and B. The three primary color signals R, G and B are converted to analog video signals by a D/A conversion circuit (not shown) and outputted from a video signal output end to the monitor 5.

In the third matrix circuit 49, (matrix coefficients of) matrix Mat3 thereof are dynamically changed by the control circuit 15 based on the respective signal intensity ratios s, t and u of the first three primary color signals R1, G1 and B1 generated by the first matrix circuit 42.

To be more specific, assuming that the matrix of two rows and three columns of the second matrix circuit 46 is Mat2 and the respective signal intensity ratios s, t and u of the first three primary color signals R1, G1 and B1 are used, matrix Mat3 is dynamically changed so as to be:

$$Mat3 = \begin{bmatrix} s & t & u \\ Mat2 \end{bmatrix}^{-1} \quad (2)$$

Here, matrix Mat2 is set, for example, as:

$$Mat2 = \begin{bmatrix} 0.701 & -0.587 & -0.114 \\ -0.299 & -0.587 & 0.886 \end{bmatrix} \quad (3)$$

where, $(\ )^{-1}$ means an inverse matrix.

Furthermore, in the present embodiment, when the endoscope image is displayed in color on the monitor 5 in the NBI mode, a color conversion setting section 50 is provided which makes a setting so that signals are color-converted and displayed to improve visibility compared to a case where actual color signals are displayed as they are.

When performing color conversion, the operator turns ON a color conversion switch (not shown) in the color conversion setting section 50 and the operation signal is outputted to the control circuit 15.

When the color conversion setting section 50 gives an instruction for performing color conversion, the control circuit 15 uses matrix Mat3 in Equation (4) below instead of using matrix Mat3 in Equation (2) with reference to matrix elements (also called "matrix coefficients") k1, k2 and k3 for performing standard color conversion stored, for example, in the table 15*a* beforehand.

$$Mat3 = M_{Trans} \cdot \begin{bmatrix} s & t & u \\ Mat2 \end{bmatrix}^{-1} = \begin{bmatrix} 0 & k1 & 0 \\ 0 & 0 & k2 \\ 0 & 0 & k3 \end{bmatrix} \cdot \begin{bmatrix} s & t & u \\ 0.701 & -0.587 & -0.114 \\ -0.299 & -0.587 & 0.886 \end{bmatrix}^{-1} \quad (4)$$

As is clear from the above table, matrix Mat3 in Equation (4) corresponds to matrix Mat3 in Equation (2) multiplied by color conversion matrix $M_{Trans}$ including color conversion matrix elements k1, k2 and k3. However, in the NBI mode, the signal intensity ratio s in Equation (3) is 0 (that is, s=0).

The operator may also be allowed to operate the color conversion setting section 50 to set the values of the color conversion matrix elements k1, k2 and k3 to be variable when performing color conversion.

Furthermore, regarding contour emphasis by the emphasis circuit 48, emphasis characteristics (whether the emphasis band should be set to a medium to low band or a medium to high band) or the like may be modified according to the types of the CCD 29 and the color separation filter 30 via the control circuit 15.

In the NBI mode in particular, if the luminance signal Yh is set to be subjected to emphasis processing, this means that processing is performed with the structure of a capillary vessel or the like near the biological surface layer emphasized, which allows an image component of interest to be clearly displayed.

Thus, the present embodiment calculates the respective signal intensity ratios s, t and u of the first three primary color signals R1, G1 and B1 as the output signals of the first matrix circuit 42 in the predetermined region Rd for each field in conjunction with a changeover between the observation modes.

When the endoscope image is displayed on the monitor 5 using the calculated signal intensity ratios s, t and u, the three primary color signals R, G and B are generated as the image signals thereof by the third matrix circuit 49 according to the color separation processing of the luminance signal Yh and the color difference signals R−Y and B−Y. That is, the present embodiment applies color separation processing that reflects the signal intensity ratios of the first three primary color signals R1, G1 and B1 through matrix calculations using matrix Mat3 of the third matrix circuit 49 to the luminance signal Yh generated by the Y/C separation circuit 37.

The endoscope apparatus 1 in such a configuration includes the CCD 29 as image pickup means for picking up an image of the interior of the body cavity, the Y/C separation circuit 37 as first color separation means for separating the image picked up by the image pickup means into a first luminance signal and first color difference signals and the first matrix circuit 42 as first color conversion means for performing conversion to first three primary color signals based on the first luminance signal and the first color difference signals.

Furthermore, the endoscope apparatus 1 includes the second matrix circuit 46 as second color conversion means for converting the output signal from the first color conversion means to a second color difference signal, the third matrix circuit 49 as second color separation means for converting the first luminance signal and the output signal from the second color conversion means to second three primary color signals and the signal intensity ratio calculation circuit 44 as signal intensity ratio calculation means for calculating an intensity ratio among the first three primary color signals outputted from the first color conversion means, and changes processing contents of the second color separation means according to the output result of the signal intensity ratio calculation means.

Figure 5:
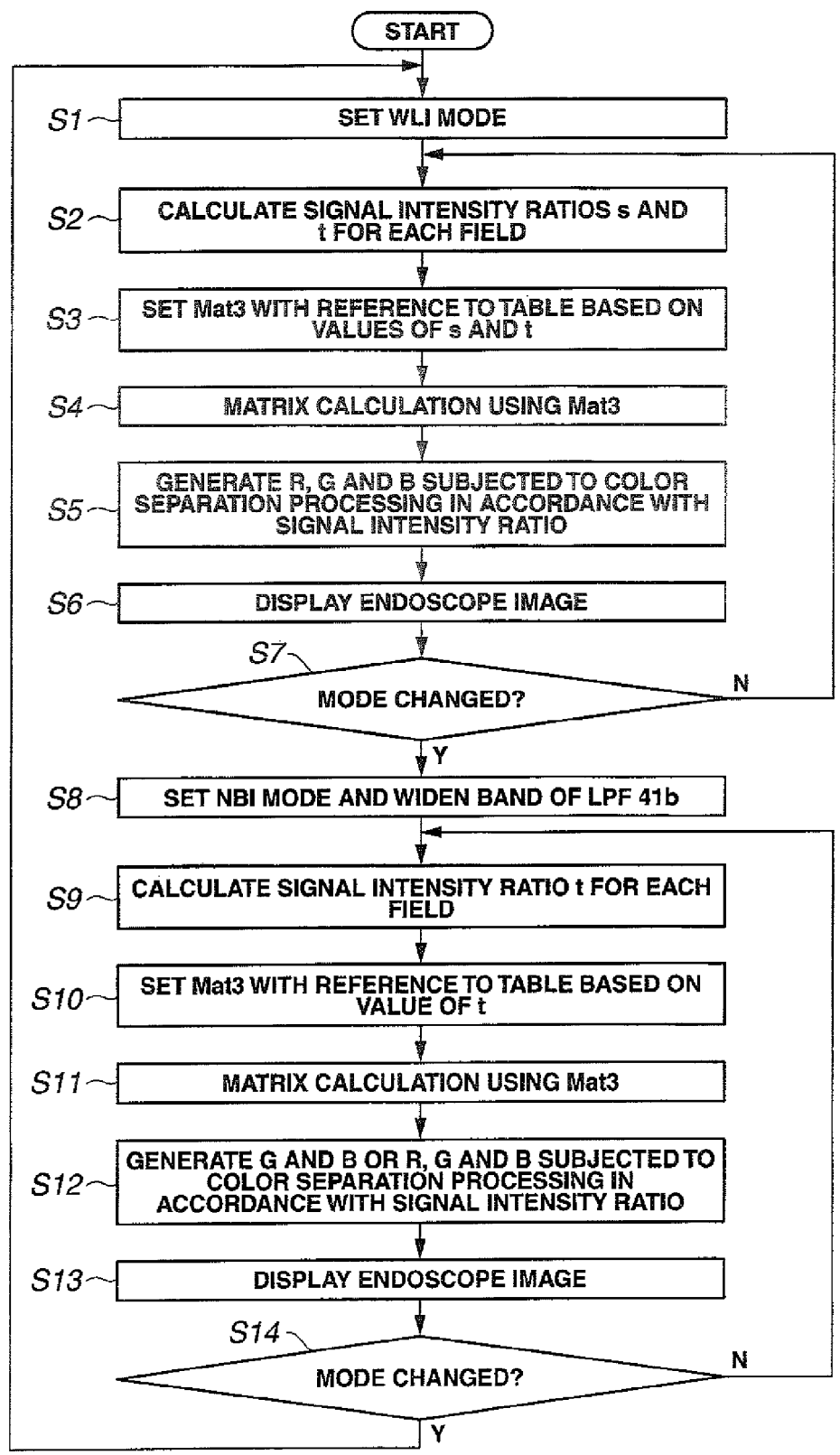
FIG. 5 is a flowchart illustrating main operation in the first embodiment.

Main operation of the present embodiment will be described below with reference to FIG. 5.

When the operator connects the endoscope 2 to the light source device 3 and the video processor 4 as shown in FIG. 1 and turns ON the power, the control circuit 15 of the video processor 4 starts initial setup processing, and as shown in step S1, the control circuit 15 causes the light source device 3 and the video processor 4 to be set in an operating mode, for example, of a WLI mode.

In this condition, the light source device 3 is set in a state in which the narrow band filter 24 is separated from the illuminating light path as shown by a solid line in FIG. 1 and the endoscope 2 is set to perform image pickup under white illuminating light. Furthermore, the sections on the video processor 4 side are also set to perform signal processing in the WLI mode.

As shown in step S2, the signal intensity ratio calculation circuit 44 in the processor 4 calculates signal intensity ratios s and t for each field.

As shown in step S3, the control circuit 15 sets matrix Mat3 of the third matrix circuit 49 with reference to the table 15a based on the signal intensity ratios s and t. In this case, the signal intensity ratio u is calculated from the condition of s+t+u=1. As shown in step S4, the third matrix circuit 49 performs matrix calculation using matrix Mat3. Through this matrix calculation, the third matrix circuit 49 generates three primary color signals R, G and B with the luminance signal Yh subjected to color separation processing in accordance with the signal intensity ratios s, t and u as shown in step S5.

As shown in step S6, the monitor 5 displays an endoscope image corresponding to the three primary color signals R, G and B. The operator performs an endoscope inspection of a tissue to be examined such as a diseased part in the body cavity while observing the endoscope image.

When attempting to observe the running state or the like of a blood vessel on the surface of the tissue to be examined in detail, the operator operates the mode changeover switch 14.

As shown in step S7, the control circuit 15 monitors whether or not the mode changeover switch 14 is operated, returns to step S2 when the mode changeover switch 14 is not operated, maintains the WLI mode, or moves to next step S8 when the mode changeover switch 14 is operated.

In step S8, the control circuit 15 changes the operating mode of the light source device 3 and the video processor 4 to the NBI mode.

To be more specific, the control circuit 15 controls the light source device 3 so as to place the narrow band filter 24 in the illuminating light path as shown by a two-dot dashed line in FIG. 1. When the narrow band filter 24 is placed in the illuminating light path, the transmission characteristic of which is shown in FIG. 2, illumination is performed using narrow band illuminating light with the narrow band pass filter characteristic portions Ga and Ba.

Furthermore, the control circuit 15 modifies the settings of the sections of the video processor 4. To be more specific, the control circuit 15 widens the band characteristic of the LPF 41b.

Furthermore, the control circuit 15 widens the signal passband characteristic of the LPF 41b, and as described above, improves the resolution of the running state of a capillary vessel and the running state of a blood vessel or the like near the surface layer obtained by the color signal of G, an image of which is picked up under illuminating light of G approximate to the luminance signal with the narrow band pass filter characteristic portion Ga.

In next step S9, the signal intensity ratio calculation circuit 44 calculates a signal intensity ratio t for each field.

As shown in next step S10, the control circuit 15 sets matrix Mat3 of the third matrix circuit 49 with reference to the table based on the signal intensity ratio t. In this case, the signal intensity ratio u is calculated from the condition of t+u=1.

As shown in step S11, the third matrix circuit 49 performs matrix calculation using matrix Mat3. The third matrix circuit 49 generates three primary color signals G and B or R, G and B in a condition in which the luminance signal Yh is subjected to color separation processing in accordance with the signal intensity ratios t and u as shown in step S12 through matrix calculation.

When the color conversion setting section 50 is OFF, the third matrix circuit 49 generates three primary color signals G and B, while when the color conversion setting section 50 is ON, the third matrix circuit 49 generates three primary color signals R, G and B.

As shown in step S13, the monitor 5 displays an endoscope image corresponding to the three primary color signals G and B or R, G and B.

While observing the endoscope image, the operator performs an endoscope inspection by setting a state in which it is easier to observe the running state of the capillary vessel near the surface of the tissue to be examined in the body cavity in more detail.

In next step S14, the control circuit 15 monitors whether or not the mode changeover switch 14 is operated, returns, when the mode changeover switch 14 is not operated, to the processing in step S9 and maintains the state in the NBI mode or returns to step S1 when the mode changeover switch 14 is operated.

According to the present embodiment operating in this way, it is possible to maintain the existing simultaneous type color image pickup function in the WLI mode and also modify processing characteristics such as the settings of coefficients of the sections in the video processor 4 in the NBI mode, and thereby secure a sufficient observation function in the NBI mode.

That is, it is possible to obtain an endoscope image with high resolution and also display the running state of the capillary vessel, an image of which is picked up under narrow band illuminating light, in a more clearly and easily identifiable manner.

Furthermore, since the present embodiment performs color separation processing also on the luminance signal Yh in accordance with the signal intensity ratios s, t and u of the first three primary color signals R1, G1 and B1 that vary depending on the object, it is possible to improve the color separation function also in the NBI mode and prevent the contrast from deteriorating in the NBI mode.

Furthermore, the present embodiment changes some processing characteristics in the signal processing system, and can thereby easily respond to both the WLI mode and NBI mode, thus providing a highly convenient and useful apparatus during an endoscope inspection.

Furthermore, by providing means for inserting/removing the narrow band filter 24 in/from the optical path in addition to illumination means of normal white light, in the light source device 3, it is also possible to easily form a light source device of narrow band light.

In the descriptions of the aforementioned first embodiment, the third matrix circuit 49 modifies matrix coefficients according to the calculation result of the signal intensity ratio of the signal intensity ratio calculation circuit 44 in both the WLI mode and the NBI mode.

As a modification example of the first embodiment, matrix coefficients of the third matrix circuit 49 may be modified (switched) according to the calculation result of the signal intensity ratio calculation circuit 44 only in the NBI mode, whereas in the WLI mode, the matrix coefficients of the third matrix circuit 49 may be set to predetermined fixed values and use the apparatus with the fixed values even when the calculation result of the signal intensity ratio of the signal intensity ratio calculation circuit 44 is different.

In such a case, operations and effects similar to those in the first embodiment are obtained in the NBI mode. On the other hand, in the WLI mode, even when matrix coefficients of the third matrix circuit 49 are fixed, it is possible to reduce influences of deterioration of the contrast due to color separation processing on the luminance signal Yh compared to the NBI mode.

When matrix coefficients of the third matrix circuit 49 are set to predetermined fixed values in the WLI mode as described above, the matrix coefficients may be set to fixed values corresponding to the calculation result of the signal intensity ratio under a predetermined condition by the signal intensity ratio calculation circuit 44 (for example, in the case of an initial setup or the case of timing at which white balancing is instructed as will be described later).

(Second Embodiment)

Figure 6:
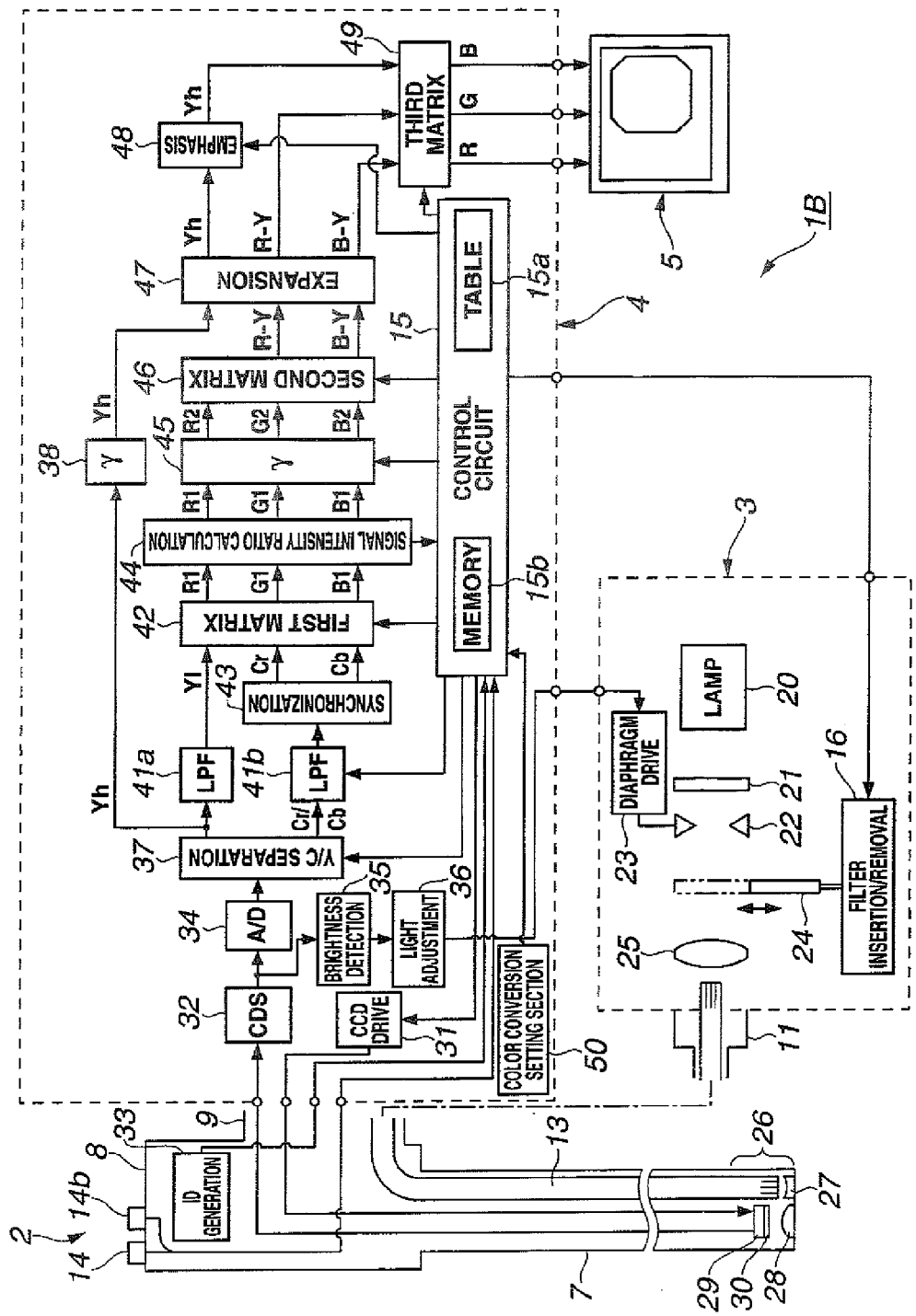
FIG. 6 is a block diagram illustrating a configuration of an endoscope apparatus according to a second embodiment of the present invention.

Next, a second embodiment of the present invention will be described. FIG. 6 is a diagram illustrating a configuration of an endoscope apparatus 1B according to a second embodiment of the present invention. The endoscope apparatus 1B corresponds to the endoscope apparatus 1 in FIG. 1 including a WB switch 14b that performs operation of instructing acquisition of white balance (abbreviated to "WB") provided, for example, in the endoscope 2. The WB switch 14b may also be provided in the video processor 4. Furthermore, the WB switch 14b may also be provided in the endoscope 2 and the video processor 4.

The WB switch 14b is operated by the operator or the like in a condition in which the endoscope 2 is set to be ready to pick up an image of a predetermined reference object such as white object provided beforehand in the WLI mode.

Furthermore, the WB switch 14b is also operated in the NBI mode in which an image of a predetermined reference object provided beforehand for the NBI mode is picked up under illumination with narrow band illuminating light.

In this case, a common reference object may be used in the WLI mode and the NBI mode or different reference objects may be used. A case will be described in the following description where a common reference object is used for simplicity of explanation.

When the operator operates this WB switch 14b, the WB switch 14b sends an instruction signal for acquiring WB to the control circuit 15. The control circuit 15 acquires information on signal intensity ratios s, t and u calculated by the signal intensity ratio calculation circuit 44 for the first three primary color signals R1, G1 and B1 at timing at which the instruction signal is inputted.

As in the case of the aforementioned embodiment, information on the signal intensity ratios s, t and u (two pieces of information when the condition of s+t+u=1 is included) is used in the WLI mode, whereas in the NBI mode, information on the signal intensity ratios t and u (one piece of information when the condition of t+u=1 is included) is used.

The control circuit 15 sets values of matrix coefficients of the third matrix circuit 49 as predetermined fixed values using the information on the signal intensity ratios s, t and u (or t and u) acquired at this timing and performs control thereafter such that the apparatus is used without modifying the values of the matrix coefficients unless the WB switch 14b is operated.

Therefore, in the present embodiment, the signal intensity ratio calculation circuit 44 has the function of generating three primary color signals (with color separation applied to the luminance signal Yh) by reflecting information on the signal intensity ratios acquired under a condition under which an image of a reference object is picked up for the third matrix circuit 49.

Furthermore, in the present embodiment, for example, the control circuit 15 has a memory 15b that stores information on the signal intensity ratios s, t and u for when the WB switch 14b is operated in the WLI mode and information on the signal intensity ratios t and u for when the WB switch 14b is operated in the NBI mode. The rest of the configuration is the same as that of the first embodiment.

Figure 7:
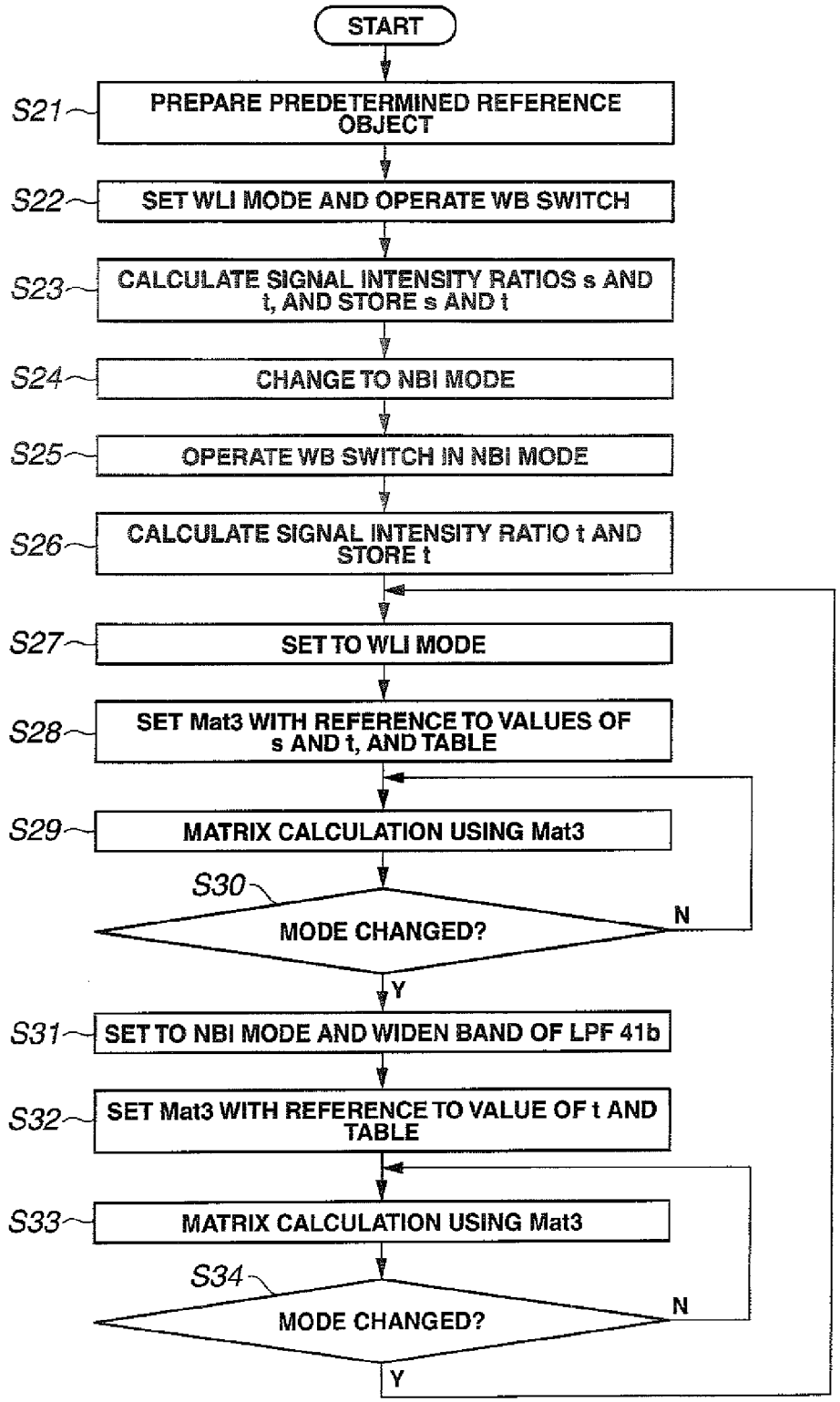
FIG. 7 is a flowchart illustrating main operation in the second embodiment.

FIG. 7 is a flowchart illustrating main operation of the present embodiment.

The operator makes an initial setting first. Thus, the operator prepares a predetermined reference object in step S21. In next step S22, the operator sets the predetermined reference object to be ready for image pickup by the endoscope 2, sets the apparatus in the WLI mode and operates the WB switch 14b.

Then, as shown in step S23, the signal intensity ratio calculation circuit 44 calculates the signal intensity ratios s and t in a field or frame when the WB switch 14b is operated and outputs the signal intensity ratios s and t to the control circuit 15. The control circuit 15 stores the values of the signal intensity ratios s and t in the memory 15b. The control circuit 15 displays on the monitor 5 the fact that the values of the signal intensity ratios s and t have been stored.

In next step S24, the operator operates the mode changeover switch 14 and selects the NBI mode. After selecting the NBI mode, the operator operates the WB switch 14b in next step S25.

As shown in step S26, the signal intensity ratio calculation circuit 44 calculates the signal intensity ratio t in a field or frame when the WB switch 14b is operated and outputs the signal intensity ratio t to the control circuit 15. The control circuit 15 stores the value of the signal intensity ratio t in the memory 15b. The control circuit 15 displays on the monitor 5 the fact that the value of the signal intensity ratio t has been stored. The initial setting is completed in this way.

Next, an endoscope inspection is started. For this purpose, the operator operates, for example, the mode changeover switch 14 and sets the apparatus in the WLI mode. The light source device 3 and the video processor 4 are set in the WLI mode.

Furthermore, as shown in step S28, the control circuit 15 sets matrix Mat3 with reference to the values of the signal intensity ratios s and t in the WLI mode from the memory 15b and the table 15a. As shown in step S29, the third matrix circuit 49 performs matrix calculation using matrix Mat3. The monitor 5 displays the endoscope image.

In step S30, the control circuit 15 monitors whether or not the mode changeover switch 14 is operated. When the mode changeover switch 14 is not operated, the control circuit 15 returns to step S29, performs matrix calculation using the same matrix Mat3, and the monitor 5 displays the endoscope image.

When the operator wants to observe the running state or the like of the blood vessel of the surface of the tissue to be examined in more detail, the operator operates the mode changeover switch 14. As shown in step S31, the light source device 3 and the video processor 4 are set in the NBI mode. The LPF 41b is changed to a wide band characteristic.

Furthermore, as shown in step S32, the control circuit 15 sets matrix Mat3 with reference to information on the signal intensity ratio t in the NBI mode from the memory 15b and the table 15a. As shown in step S32, the third matrix circuit 49 performs matrix calculation using matrix Mat3. The monitor 5 then displays the endoscope image.

Furthermore, as shown in step S33, the control circuit 15 monitors whether or not a mode changeover operation is performed. When the mode changeover operation is not performed, the control circuit 15 returns to step S32 and performs matrix calculation using the same matrix Mat3. The monitor 5 displays the endoscope image. On the other hand, when the mode changeover operation is performed, the control circuit 15 returns to step S27, sets the apparatus in the WLI mode and repeats the aforementioned processing.

The present embodiment displays an endoscope image corresponding to a case where color separation processing is applied which reflects the signal intensity ratio in a state of picking up an image of a predetermined reference object for which the WB switch 14b is operated.

Thus, the present embodiment performs color separation processing corresponding to a state of picking up an image of a predetermined reference object, and is therefore suitable for use in making a chronological comparison in the state of cure with respect to the same lesioned part or the like.

Furthermore, the present embodiment selects and sets a predetermined reference object in the NBI mode according to a tissue to be examined, and can thereby also display the capillary vessel or the like of the tissue to be examined with higher contrast.

Furthermore, as in the case of the first embodiment, the present embodiment also applies color separation processing to the luminance signal Yh in the case of a reference object and generates three primary color signals used for a display as an endoscope image, and can thereby prevent the contrast of the endoscope image displayed on the monitor 5 from deteriorating.

The operating modes in the first embodiment and the second embodiment may be made selectable. For example, the operating mode of the second embodiment may be made selectable in the WLI mode, while the operating mode of the first embodiment may be made selectable in the NBI mode. Furthermore, the operating modes may be made selectable in the reverse way.

(Third Embodiment)

Figure 8:
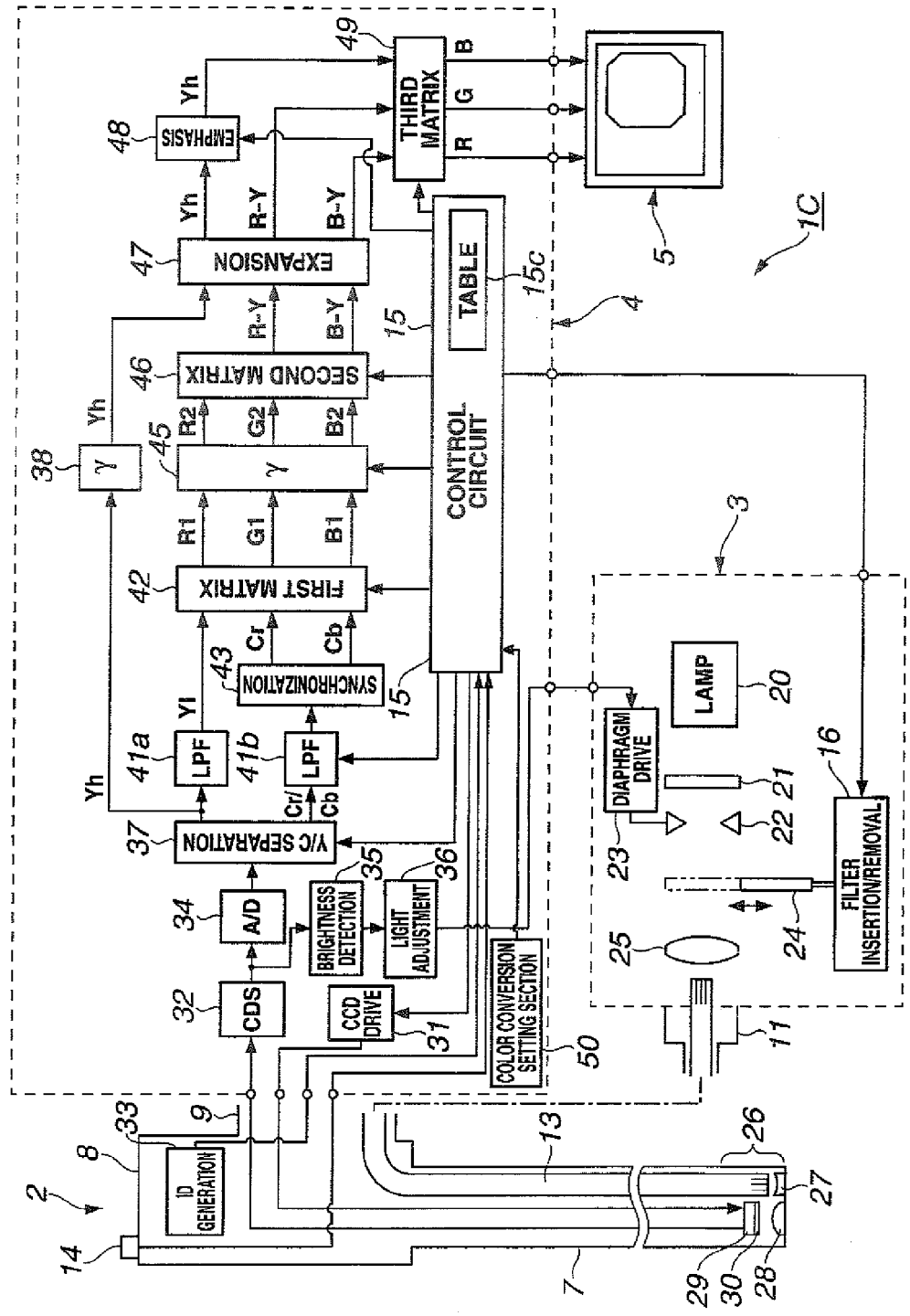
FIG. 8 is a block diagram illustrating a configuration of an endoscope apparatus according to a third embodiment of the present invention.

Next, a third embodiment of the present invention will be described. FIG. 8 illustrates a configuration of an endoscope apparatus 1C according to the third embodiment of the present invention. The endoscope apparatus 1C in the present embodiment corresponds to the endoscope apparatus 1 shown in FIG. 1 without the signal intensity ratio calculation circuit 44.

The endoscope apparatus 1C of the present embodiment is configured to change matrix coefficients of the first matrix circuit 42 and the third matrix circuit 49 according to the type such as a spectral sensitivity characteristic of the color separation filter 30 of the CCD 29 mounted on the endoscope 2 and white light or narrow band light emitted from the illumination lens 27 via the light source device 3 or the light guide 13 of the endoscope 2, that is, the observation mode.

For this reason, for example, the control circuit 15 in the video processor 4 sets matrix Mat3 of the third matrix circuit 49 with reference to, for example, a table 15c provided in the control circuit 15 according to a combination of the result of a decision on the type of the CCD 29 based on the ID from the ID generation section 33 of the endoscope 2 and an observation mode.

This table 15c stores data for setting (matrix coefficients of) matrix Mat3 according to the combination of the spectral sensitivity characteristic of the color separation filter 30 of the CCD 29 and the observation mode. The matrix of the second matrix circuit 46 has fixed values.

To be more specific, the matrix coefficients of matrix Mat3 are calculated (set) based on a ratio of an integral value of a spectral product as the product of various spectral characteristics from the illumination system to the image pickup system of wavelength bands of R, G and B (or G and B) in a luminance signal.

With such a setting, even when the spectral sensitivity characteristic of the CCD 29 mounted in the endoscope 2 used as the endoscope apparatus, the spectral characteristic of illuminating light of the light source device 3 and the spectral characteristic of the illuminating light transmission means of the light guide 13 for transmitting illuminating light from the light source device 3 and outputting the light to a tissue to be examined in the body cavity from the distal end portion thereof as illuminating light are different, appropriate color separation is applied to the luminance signal Yh accordingly. The rest of the configuration is the same as that of the first embodiment.

Figure 9:
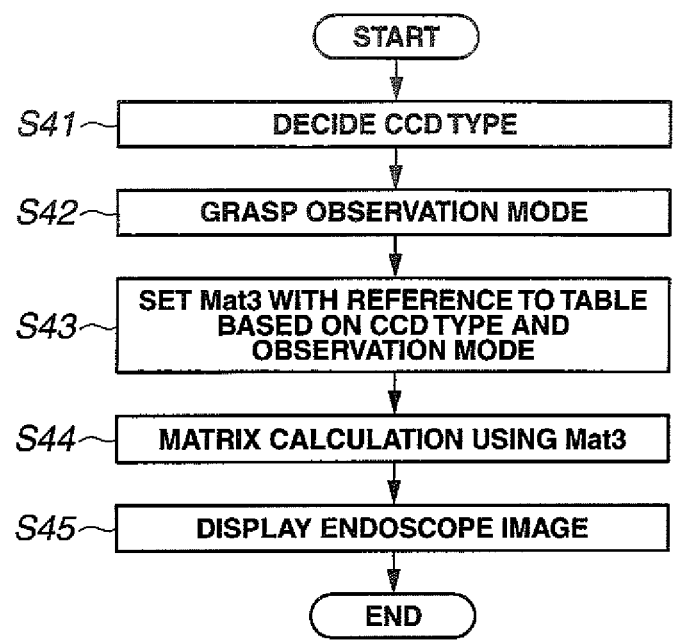
FIG. 9 is a flowchart illustrating main operation in the third embodiment.

Schematic operation of the present embodiment is as shown in FIG. 9. In first step S41, the control circuit 15 decides the type of the CCD 29 from the ID by the ID generation section 33 of the endoscope 2.

Furthermore, in step S42, the control circuit 15 grasps the observation mode set (selected) according to a switch operation of the mode changeover switch 14.

In step S43, the control circuit 15 sets matrix Mat3 of the third matrix circuit 49 with reference to the table 15c based on the type of the CCD 29 and the observation mode.

In step S44, the third matrix circuit 49 performs matrix calculation using matrix Mat3 and generates an image signal of the endoscope image to be displayed on the monitor 5. As shown in step S45, this endoscope image is displayed on the monitor 5.

The present embodiment performs matrix calculation by setting matrix Mat3 of the third matrix circuit 49 according to an integral ratio of the spectral product of various spectral characteristics from the illumination system to the image pickup system.

Therefore, even when the spectral characteristics of the CCD 29, the light source device 3, the light guide 13 or the like mounted on the endoscope 2 used as the endoscope apparatus are different, color separation corresponding to those spectral characteristics is applied to the luminance signal Yh. Therefore, the color separation function improves and it is possible to prevent the contrast from deteriorating.

A case has been described above where the type of the CCD 29 is decided (detected) and further matrix coefficients of matrix Mat3 of the third matrix circuit 49 are set from the table 15c with reference to the observation mode. As a modification example of the present embodiment, each endoscope 2 may be configured to store information for determining the CCD 29 mounted on the endoscope 2 and matrix Mat3 for each observation mode.

In this case, the control circuit 15 refers to the table 15c based on the information and determines matrix coefficients of corresponding matrix Mat3. The third matrix circuit 49 performs matrix calculation using matrix Mat3.

As a specific example of the information for determining matrix Mat3, for example, a case will be described where a plurality of bits making up the ID generated by the ID generation section 33 include this information. That is, suppose a plurality of predetermined bits in the ID include information for determining matrix coefficients of matrix Mat3.

Figure 10:
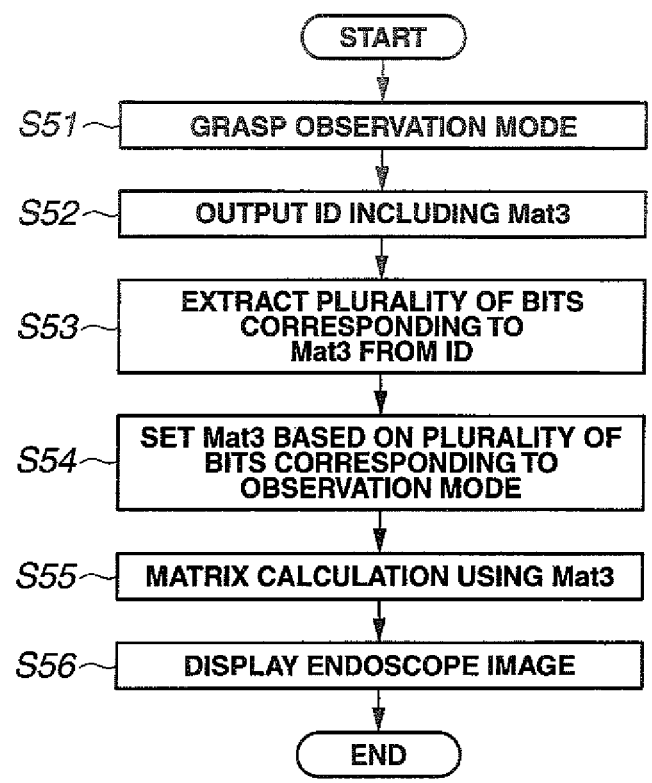
FIG. 10 is a flowchart illustrating main operation in a modification example of the third embodiment.

Schematic operation in the case of this modification example is as shown in FIG. 10.

In first step S51, the control circuit 15 grasps an observation mode set (selected) according to a switch operation by the mode changeover switch 14.

In next step S52, the ID generation section 33 of the endoscope 2 outputs an ID including information that determines matrix Mat3 to the control circuit 15 of the video processor 4.

Furthermore, in step S53, the control circuit 15 extracts data of a plurality of bits that determine matrix coefficients of matrix Mat3 for each observation mode from this ID.

In step S54, the control circuit 15 sets matrix Mat3 of the third matrix circuit 49 with reference to the table 15c based on the data of a plurality of bits corresponding to the current observation mode.

In next step S55, the third matrix circuit 49 performs matrix calculation using matrix Mat3 and generates an image signal of the endoscope image to be displayed on the monitor 5. As shown in step S56, the endoscope image is displayed on the monitor 5.

The present modification example has substantially the same operations and effects as those of the above-described third embodiment.

An embodiment configured by partially combining the aforementioned embodiments also belongs to the present invention. The aforementioned first to third embodiments have described a case with the observation modes of the WLI mode and the NBI mode, but the present invention may further be applied to an observation mode using a fluorescent mode in which fluorescent observation is performed using excitation light.

For example, when the mode is changed to the fluorescent mode, matrix coefficients corresponding to the first matrix circuit may be changed according to spectral characteristics of the fluorescent light incident on the image pickup means of the endoscope and characteristics of the color separation filter in the image pickup means and the matrix coefficients of the matrix circuit corresponding to the third matrix circuit may also be changed based on the signal intensity ratio of the output signal of the circuit corresponding to the first matrix circuit and color separation processing may be applied to the luminance signal Yh.

The present invention is not limited to the above-described embodiments, but various modifications or alterations or the like can be made without departing from the spirit and scope of the present invention.

What is claimed is:

1. An endoscope apparatus comprising:
an illumination section that illuminates a body cavity interior;
an image pickup section that picks up an image of return light from the body cavity interior under illumination by the illumination section;
an illumination changeover section that is capable of switching between white light and illuminating light of narrow band wavelength illuminated from the illumination section;
a first color separation section that separates the image picked up by the image pickup section into a first luminance signal and a first color difference signal;
a first color conversion section that converts the signals to first three primary color signals based on the first luminance signal and the first color difference signal;
a second color conversion section that converts an output signal from the first color conversion section to a second color difference signal;
a signal intensity ratio calculation section that calculates an intensity ratio among the first three primary color signals outputted from the first color conversion section:
a table for storing matrix coefficients used for performing color separation matrix calculation on each of the first luminance signal obtained by separation in the first color separation section and the second color difference signal obtained by conversion in the second color conversion section;
a control section that switches the matrix coefficients stored in the table, based on the intensity ratio calculated in the signal intensity ratio calculation section; and
a second color separation section that performs color separation matrix calculation on each of the first luminance signal obtained by the separation in the first color separation section and the second color difference signal obtained by conversion in the second color conversion section based on the matrix coefficients switched in the control section, to convert the signals to second three primary color signals.

2. The endoscope apparatus according to claim 1, wherein when the image pickup section picks up an image under illumination with white light by the illumination section, a first matrix coefficient with which the first color conversion section performs conversion is changed according to spectral characteristics of light incident on the image pickup section.

3. The endoscope apparatus according to claim 2, wherein when the image pickup section picks up an image under illumination by the illumination section with illuminating light of a predetermined narrow band wavelength, the matrix coefficient with which the second color separation section performs color separation conversion is changed according to an output result of the signal intensity ratio calculation section, and when the image pickup section picks up an image under illumination by the illumination section with white light, the matrix coefficient with which the second color separation section performs color separation conversion is set to a fixed value.

4. The endoscope apparatus according to claim 2, wherein when the image pickup section picks up an image under illuminating light of a predetermined narrow band wavelength, a passband of a filter that limits the passband with respect to the first color difference signal is set to a wider band than when the image pickup section picks up an image under illuminating light of white light.

5. The endoscope apparatus according to claim 1, wherein when the image pickup section picks up an image under illumination with illuminating light of a predetermined narrow band wavelength by the illumination section, a first matrix coefficient with which the first color conversion section performs conversion is changed according to spectral characteristics of light incident on the image pickup section.

6. The endoscope apparatus according to claim 5, wherein when the illumination section performs illumination with illuminating light of a predetermined narrow band wavelength, a second matrix coefficient with which the second color conversion section performs conversion is set to a fixed value and the matrix coefficient with which the second color separation section performs conversion is changed.

7. The endoscope apparatus according to claim 5, wherein when the image pickup section picks up an image under illuminating light of a predetermined narrow band wavelength, a passband of a filter that limits the passband with respect to the first color difference signal is set to a wider band than when the image pickup section picks up an image under illuminating light of white light.

8. The endoscope apparatus according to claim 1, wherein the signal intensity ratio calculation section calculates an intensity ratio among the first three primary color signals for each field or each frame by the image pickup section and the second color separation section dynamically changes the matrix coefficient with which color separation is converted for each field or each frame according to an output result of the intensity ratio by the signal intensity ratio calculation section.

9. The endoscope apparatus according to claim 1, wherein the signal intensity ratio calculation section calculates an intensity ratio among the first three primary color signals at a timing instructed in a situation in which an image of a predetermined reference object is picked up and the second color separation section uses the matrix coefficient with which color separation conversion is performed as a fixed value based on an output result of the intensity ratio calculated at the timing.

10. The endoscope apparatus according to claim 1, wherein the table stores the matrix coefficients as a value based on a ratio of a spectral product of each of wavelength bands of the first luminance signal, the spectral product being as a product of spectral characteristics from the illumination section to the image pickup section.

* * * * *